United States Patent
DiPalma et al.

(10) Patent No.: US 6,610,038 B1
(45) Date of Patent: Aug. 26, 2003

(54) BODY-CONFORMING BLADDER INSERT FOR AN ABSORBENT ARTICLE WITH A BODY-FITTING MECHANISM

(75) Inventors: Joseph DiPalma, Neenah, WI (US); Alexander M. Schmidt-Foerst, Woodstock, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/387,725

(22) Filed: Aug. 31, 1999

(51) Int. Cl.$^7$ .................................................. A61F 13/15
(52) U.S. Cl. ............................ 604/385.12; 604/385.17
(58) Field of Search .................................. 604/358, 366, 604/370, 381, 385.01, 385.12, 385.17, 385.22

(56) References Cited

U.S. PATENT DOCUMENTS

| | | |
|---|---|---|
| 3,512,528 A | 5/1970 | Whitehead et al. |
| 3,525,055 A | 8/1970 | Mrozek |
| 3,713,930 A | 1/1973 | Levrini et al. |
| 3,812,001 A | 5/1974 | Ryan |
| 3,881,491 A | 5/1975 | Whyte |
| 3,921,232 A | 11/1975 | Whyte |
| 4,055,180 A | 10/1977 | Karami |
| 4,633,597 A | 1/1987 | Shiang |
| 4,723,953 A | 2/1988 | Rosenbaum et al. |
| 4,964,858 A | 10/1990 | Livny |
| 5,023,128 A | 6/1991 | Fatool |
| 5,082,723 A | 1/1992 | Gross et al. |
| 5,150,707 A * | 9/1992 | Anderson ................... 128/402 |
| 5,171,302 A | 12/1992 | Buell |
| 5,178,139 A * | 1/1993 | Angelillo et al. ............ 128/403 |
| 5,229,186 A | 7/1993 | Tribble et al. |
| 5,277,180 A * | 1/1994 | Angelillo et al. ............ 607/114 |
| 5,300,055 A | 4/1994 | Buell |
| 5,300,103 A * | 4/1994 | Stempel et al. ............. 607/108 |
| 5,324,278 A * | 6/1994 | Visscher et al. .......... 604/385.1 |
| 5,330,459 A | 7/1994 | Lavon et al. |
| 5,376,067 A | 12/1994 | Daneshvar |
| 5,520,674 A | 5/1996 | Lavon et al. |
| 5,582,604 A | 12/1996 | Ahr et al. |
| 5,591,150 A * | 1/1997 | Olsen et al. ............ 604/385.01 |
| 5,609,588 A * | 3/1997 | DiPalma et al. ............. 604/369 |
| 5,643,241 A | 7/1997 | Ahr et al. |
| 5,674,214 A * | 10/1997 | Visscher et al. .......... 604/385.1 |
| 5,702,375 A * | 12/1997 | Angelillo et al. ........... 604/358 |
| 5,728,446 A | 3/1998 | Johnston et al. |
| 5,733,274 A * | 3/1998 | Osborn, III ............... 604/385.1 |
| 5,853,401 A * | 12/1998 | Mayer et al. ................ 604/378 |
| 5,876,393 A | 3/1999 | Ahr et al. |
| 5,891,125 A | 4/1999 | Plumley |
| 5,906,879 A | 5/1999 | Huntoon et al. |
| 5,928,184 A * | 7/1999 | Etheredge et al. ............ 604/15 |
| 5,961,508 A * | 10/1999 | Mayer et al. ............. 604/385.1 |
| 6,180,847 B1 | 1/2001 | Ahr et al. |
| 6,193,701 B1 * | 2/2001 | Van Gompel et al. .. 604/385.01 |

FOREIGN PATENT DOCUMENTS

| | | |
|---|---|---|
| DE | 35 12 859 | 10/1986 |
| DE | 35 17 192 | 11/1986 |
| EP | 738 505 | 10/1996 |
| EP | 779 065 | 6/1997 |

* cited by examiner

*Primary Examiner*—Weilun Lo
*Assistant Examiner*—Jacqueline F Stephens
(74) *Attorney, Agent, or Firm*—Pauley Petersen Kinne & Erickson

(57) ABSTRACT

An absorbent article having a multi-layer material having a front section, a back section and an intermediate section connecting the front section and the back section, wherein the multi-layer material comprises a topsheet, a backsheet and an absorbent layer disposed between the topsheet and the backsheet. At least one resilient fluid-filled chamber is disposed in the absorbent layer or between at least a portion of the absorbent layer and the backsheet. A body-fitting mechanism is provided which is activatable by application of a force to the resilient fluid-filled chamber.

21 Claims, 8 Drawing Sheets

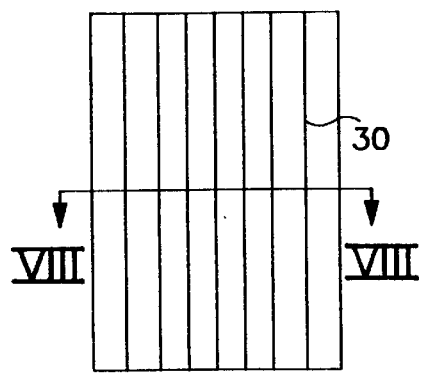
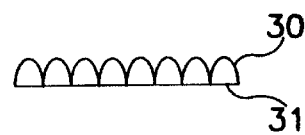
FIG. 8A
FIG. 8B
FIG. 7
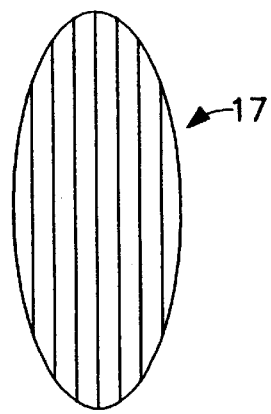
FIG. 9A
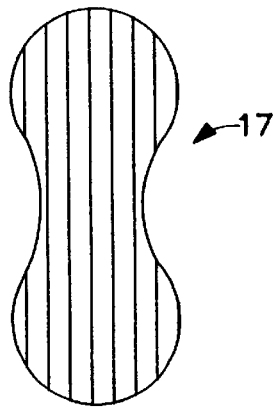
FIG. 9B
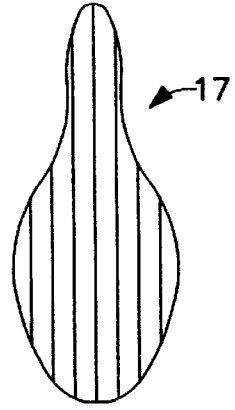
FIG. 9C
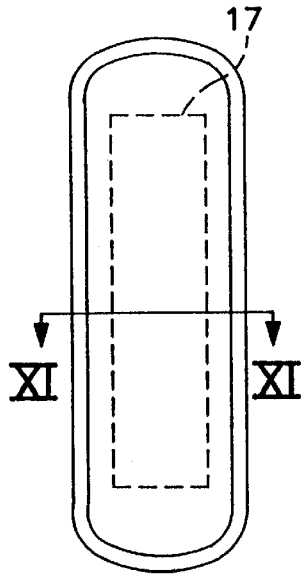
FIG. 10A
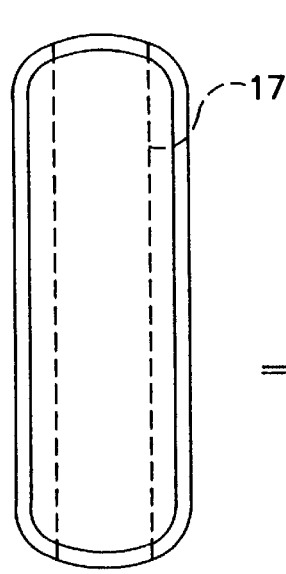
FIG. 10B
FIG. 11

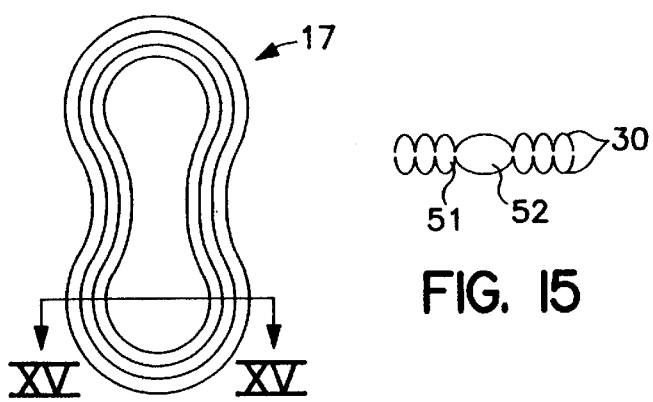
FIG. 14
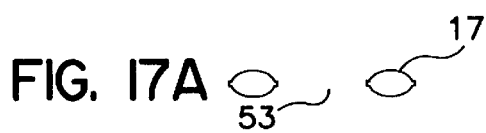
FIG. 15
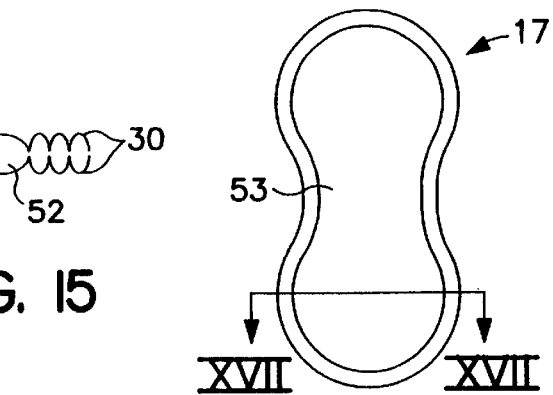
FIG. 16

FIG. 17B
FIG. 17C
FIG. 17D
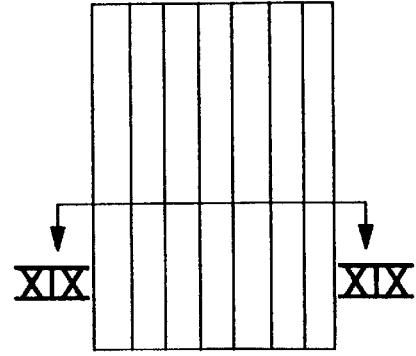
FIG. 18
FIG. 19
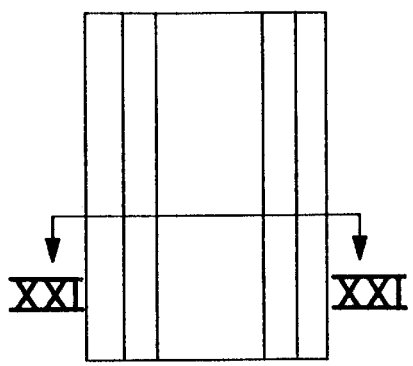
FIG. 20
FIG. 21
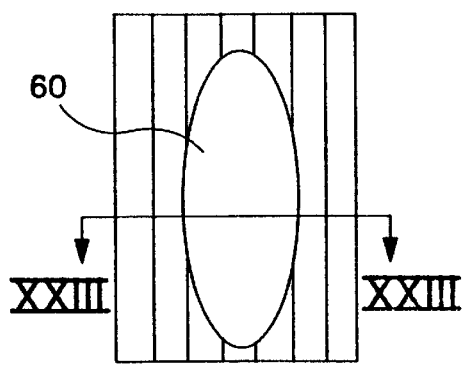
FIG. 22
FIG. 23

BODY-CONFORMING BLADDER INSERT FOR AN ABSORBENT ARTICLE WITH A BODY-FITTING MECHANISM

BACKGROUND OF THE INVENTION

Field of the Invention

This invention relates to a personal care absorbent article such as a diaper, incontinence garment and feminine care product such as sanitary napkins and panty liners. More particularly, this invention relates to personal care absorbent articles comprising a resilient fluid-filled chamber, also herein referred to as a bladder insert, which conforms while retaining much of its volume in order to generate intimate contact between the absorbent article and the wearer for improved intake of bodily discharges. The essence of the concept of this invention is that the resilient fluid-filled chamber allows the pressure to be equalized across the absorbent article surface, adapting to the dynamics of the wearer's activity. For example, as the person is seated, the pressure imparted against the seat is transferred to other portions to help press the absorbent article against the body. The resilient fluid-filled chamber can then be used to trigger a body-fitting mechanism.

The mechanical properties of the bladder insert are characterized by very high resiliency in dry and wet conditions. These resilient properties, which are mainly dependent on the pressure in the chambers and the two-dimensional arrangement of the chambers, minimize pad deformation when in use. In addition, the resilient inserts insure excellent body conformance by allowing the material to mold reversibly into the various shapes of a multitude of use conditions.

In addition to body conformance, the bladder can be used as a means for enhancing intake and distribution of bodily discharges.

SUMMARY OF THE INVENTION

It is one object of this invention to provide an absorbent article which conforms to the body of the wearer.

It is another object of this invention to provide an absorbent article which conforms to the body of the wearer and promotes the intake and distribution of bodily fluid discharges.

It is yet another object of this invention to provide an absorbent article which, although conformable to the body of the wearer, has the capability of returning substantially to a variety of use shapes.

These and other objects of this invention are addressed by an absorbent article comprising a multi-layer material having a front section, a back section and an intermediate section connecting the front section and the back section. The multi-layer material comprises a top sheet, a back sheet and an absorbent layer disposed between the top sheet and the back sheet. At least one resilient fluid-filled chamber in operable communication with at least one body-fitting mechanism is disposed one of in the absorbent layer and between at least a portion of the absorbent layer and the back sheet. The resilient fluid-filled chamber, or bladder insert, is a sealed compartment between a generally upper and a generally lower layer of material which is impermeable to its contents. The fluid impermeable material is a material selected from a group consisting of thermoplastics, elastomers, polyurethane films, coated papers and combinations thereof. In accordance with one embodiment of this invention, the fluid impermeable material comprises polyethylene and/or polypropylene.

Suitable fluids for use in the resilient fluid-filled chamber include water, air, gelatins, hydrogels, colloids, suspensions and combinations thereof.

As will be seen, the fluid-filled chamber of this invention lends itself to a plethora of embodiments and, thus, applications.

BRIEF DESCRIPTION OF THE DRAWINGS

These and other objects and features of this invention will be better understood from the following detailed description taken in conjunction with the drawings wherein:

FIG. 7 is a plan view of a multi-chamber bladder insert in accordance with one embodiment of this invention;

FIGS. 8A and 8B are cross-sectional views of the bladder insert of FIG. 7 taken along the line VIII—VIII;

FIGS. 9A, 9B and 9C are plan views of various embodiments of a multi-chamber bladder insert in accordance with this invention;

FIGS. 10A and 10B are plan views of an absorbent article having a bladder insert;

FIG. 11 is a cross-sectional view of the absorbent article of FIG. 10A in accordance with one embodiment of this invention taken along the line XI—XI;

FIG. 14 is a plan view of a bladder insert in accordance with one embodiment of this invention;

FIG. 15 is a cross-sectional view of the bladder insert of FIG. 14 taken along the line XV—XV;

FIG. 16 is a plan view of a bladder insert having an open center area in accordance with one embodiment of this invention;

FIGS. 17A, 17B, 17C and 17D are cross-sectional views of the bladder insert of FIG. 16 taken along the line XVII—XVII alone or in combination with other elements of an absorbent article in accordance with this invention;

FIG. 18 is a plan view of a bladder insert for an absorbent article in accordance with one embodiment of this invention;

FIG. 19 is a cross-sectional view of the bladder insert of FIG. 18 taken along the line XIX—XIX;

FIG. 20 is a plan view of a bladder insert for an absorbent article in accordance with one embodiment of this invention;

FIG. 21 is a cross-sectional view of the bladder insert of FIG. 20 taken along the line XXI—XXI;

FIG. 22 is a plan view of a bladder insert for an absorbent article in accordance with one embodiment of this invention;

FIG. 23 is a cross-sectional view of the bladder insert of FIG. 22 taken along the line XXIII—XXII;

DETAILED DESCRIPTION OF PREFERRED EMBODIMENTS

The invention disclosed herein is an absorbent article such as a diaper, incontinence garment or sanitary pad or napkin comprising a resilient fluid-filled chamber (bladder insert) which conforms in response to the body of the wearer while retaining much of its volume in order to generate intimate contact between the absorbent article and the wearer for improved intake and management of bodily discharges. More particularly, the bladder insert allows pressure to be equalized across the absorbent article surface, adapting to the dynamics of the wearer's activity. For example, for a seated person wearing an absorbent article in accordance with this invention, the pressure imparted against the seat of the article is transferred to other portions of the bladder insert to aid in pressing the absorbent article against the wearer's body.

The mechanical properties of the bladder insert are characterized by very high resiliency in dry and wet conditions. These resiliency properties, which are mainly dependent on the pressure in the fluid-filled chamber(s) forming the bladder insert and the two-dimensional arrangement of the chamber(s), minimize deformation of the absorbent article. In addition, the resiliency of the bladder insert ensures good body conformance by allowing the material of the bladder insert and, thus, the absorbent article to mold reversibly into the various shapes of a multitude of use conditions.

Yet a further benefit derived from the use of a bladder insert in an absorbent article in accordance with this invention is that the bladder insert adds bulk to the article without significant cost while simultaneously providing a lighter article compared to conventional articles of comparable bulk.

Figure 1:
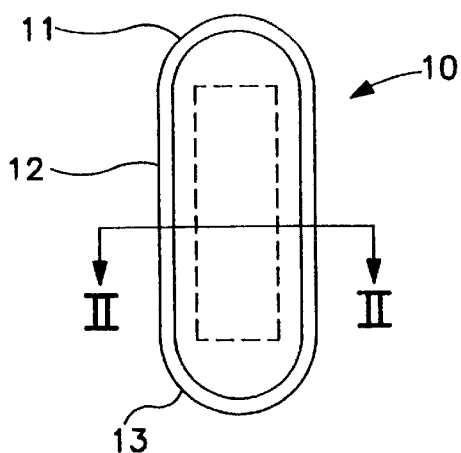
FIG. 1 is a plan view of an absorbent article comprising a bladder insert in accordance with one embodiment of this invention.
Figure 2:
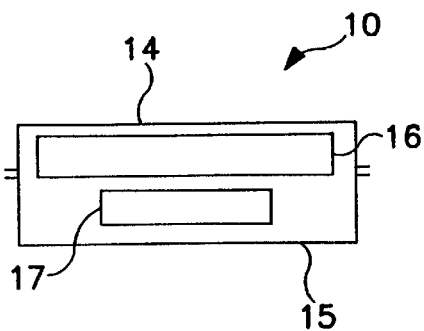
FIG. 2 is a cross-sectional view of the absorbent article of FIG. 1 taken along the line II—II.

An absorbent article 10 in accordance with one embodiment of this invention as shown in FIGS. 1 and 2 comprises a multi-layer material having a front section 11, a back section 13 and an intermediate section 12 connecting said front section 1 1 and said back section 13, said multi-layer material comprising a topsheet 14, a backsheet 15 and an absorbent layer 16 disposed between said topsheet 14 and said backsheet 15, and at least one fluid-filled chamber or bladder insert 17 disposed between at least a portion of said absorbent layer 16 and said backsheet 15.

Figure 4:
FIG. 4 is a cross-sectional view of the bladder insert shown in FIG. 3 taken along the line IV—IV.
Figure 6:
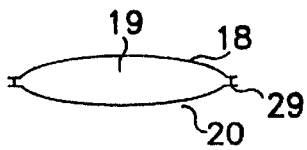
FIG. 6 is a cross-sectional view of the bladder insert of FIG. 5A taken along the line VI—VI.

Bladder insert 17, as shown in FIGS. 4 and 6 is a sealed compartment 19 between a generally upper material layer 18 and a generally lower material 20, which material is impermeable to its contents. The bladder insert material may be a coated structure or a polymer film. Materials suitable for formation of the bladder insert 17 preferably are selected from the group consisting of polyurethane films, thermoplastics, elastomers, coated papers and combinations thereof. Polyethylene or polypropylene may be used; however, an elastic material such as polyurethane is preferred due to its ability to conform to the body of the wearer and retain its volume for good anatomical fit. The outer surface of the bladder insert may be coated with a material, for example a surfactant for enhancing fluid distribution.

Fluids for filling the bladder insert may be liquids, gels or gases. Liquid fill materials have the benefit of low compressibility; gels have the benefit of a slow rate of conformability; and gases, for example air, have the benefit of being low in cost. Suitable materials with which to fill the bladder inserts are selected from the group consisting of water, air, gelatins, hydrogels, colloids, suspensions and combinations thereof.

Figure 3:
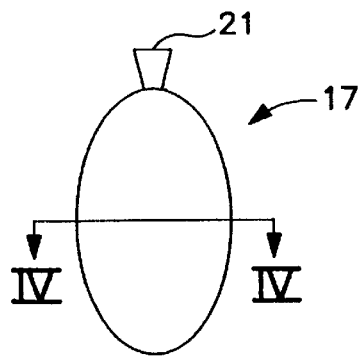
FIG. 3 is a plan view of a bladder having blowing means for inflating the bladder insert in accordance with one embodiment of this invention.
Figure 5A:
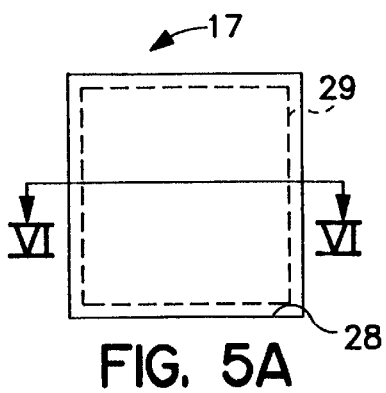
FIGS. 5A and 5B are plan views of a bladder insert in accordance with one embodiment of this invention.
Figure 5B:
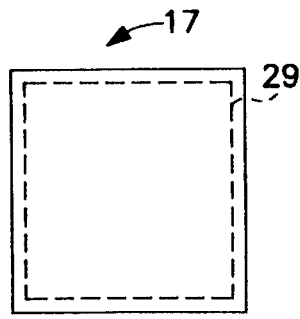

The bladder inserts for absorbent articles in accordance with this invention may be produced by a variety of methods. As shown in FIG. 3, bladder insert 17 may be made of a single material formed by blowing through fluid inlet 27 much like a toy balloon is inflated. In accordance with the embodiment shown in FIG. 5A, bladder insert 17 is formed by folding a single piece of bladder material onto itself along folded edge 28 and then sealingly bonding the folded bladder material along the remaining three sides, forming bonds 29. In accordance with another embodiment as shown in FIG. 5B, bladder insert 17 is formed by two pieces of bladder material which are generally coextensive and peripherally, sealingly bonded to each other, forming a peripheral seal. Sealing or bonding in accordance with the embodiments shown in FIGS. 5A and 5B can be accomplished by any suitable method known to those skilled in the art. Preferred sealing or bonding methods include heat sealing, ultrasonic bonding, thermal bonding, and the use of adhesives.

FIG. 7 is a plan view of a bladder insert in accordance with one embodiment of this invention wherein at least one face of the bladder insert comprises at least one pleat 30. As shown in FIG. 8A, in accordance with one embodiment of this invention, one face of the bladder insert is pleated and the other face is a rigid flat structure 31 resulting in a more controlled surface shape. In accordance with the embodiment shown in FIG. 8B, both faces of bladder insert 17 are pleated. Pleats may be formed by passing the bladder insert over a series of heated parallel wires, rollers or plates resulting in bonding of the two materials of the bladder insert to each other and formation of a plurality of individual resilient fluid-filled chambers within the bladder insert.

As shown in FIGS. 9A, 9B and 9C, bladder insert 17 may have a variety of shapes depending upon the absorbent article design requirements. In accordance with one embodiment, bladder insert 17 is square or rectangular in shape. In accordance with another embodiment, bladder insert is oval in shape (FIG. 9A). In accordance with yet another embodiment, bladder insert 17 has an hourglass shape (FIG. 9B). And, in accordance with yet another embodiment, bladder insert 17 may have an asymmetrical shape, such as the pear shape shown in FIG. 9C, to match body features.

Bladder insert 17 may be a variety of sizes depending upon the absorbent article in which it is employed. For example, it may occupy the full area of the absorbent product such as in the case of a regular maxipad. Or, as shown in FIGS. 10A and 10B, bladder insert 17 may be shorter and/or narrower than the absorbent article to minimize the thickness at the sides and ends of the article. In accordance with one embodiment of this invention, bladder insert 17 may be disposed around the perimeter of the absorbent article, such as in the case of a diaper, to provide sealing against the body to prevent leakage off the article. The seals may be continuous or at different intervals along the perimeter of the absorbent article.

Figure 13A:
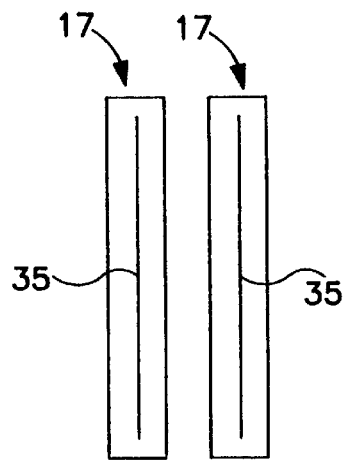
Figure 13B:
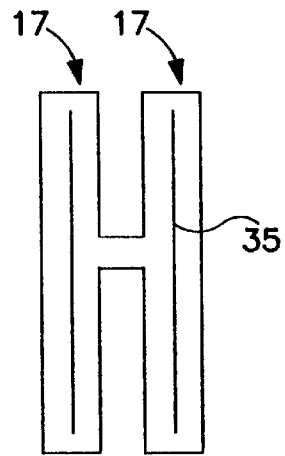

In accordance with one embodiment of the absorbent article of this invention, multiple bladder inserts may be employed at several areas around the article. For example, as shown in FIG. 13A, separate bladder inserts 17 may be disposed along each side of the absorbent article. In such cases, it will be apparent that, if desired, each individual bladder insert employed in the absorbent article may have a different pressure. Alternatively, they may be interconnected to one another as shown in FIG. 13B.

In accordance with another embodiment of this invention, bladder insert 17 is constructed of one or more materials added into the absorbent structure. As shown in FIG. 11, bladder insert 17 is laminated/bonded to an existing polymer outer baffle 34.

Figure 17A:
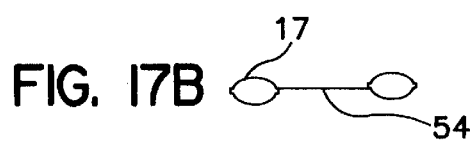

FIG. 14 is a plan view of a body-conforming bladder insert having an oval shape with a narrowed center portion. As shown in FIG. 15, this body-conforming bladder insert comprises a plurality of pleats 30 on both faces of the bladder insert and the chambers 51, 52 are of different cross-sectional areas. In the embodiment shown in FIGS. 16 and 17A, bladder insert 17 is also in an oval shape with a narrowed center portion, but unlike the bladder insert of FIG. 15, the center region 53 is open. FIG. 17B shows a cross-sectional view of the bladder insert of FIG. 16 wherein bladder material 54 spans across the center region 53. In FIGS. 17C and 17D, additional materials are shown spanning the center region on one or both faces of bladder insert 17.

Figure 12A:
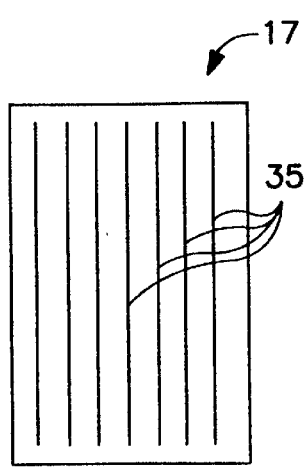
FIGS. 12A, 12B, 12C, 12D, 13A and 13B are plan views of bladder inserts in accordance with this invention comprising internal baffles.
Figure 12B:
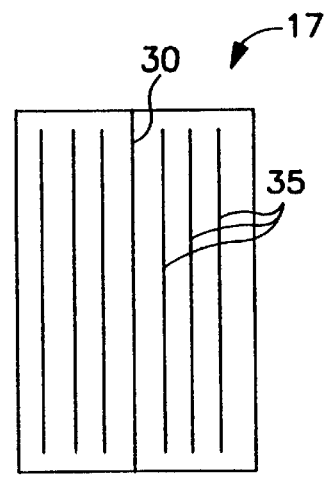
Figure 12C:
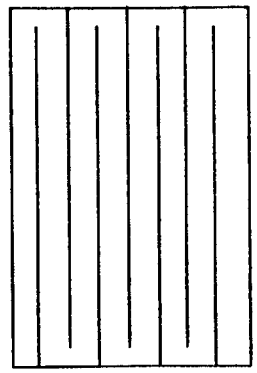
Figure 12D:
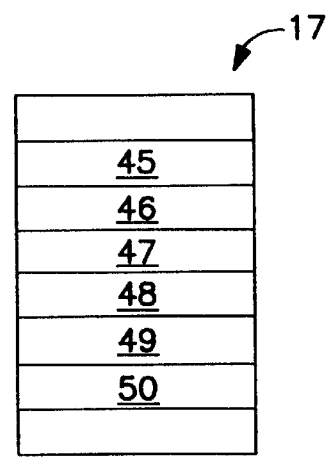

As previously stated, in accordance with one embodiment of this invention, bladder insert 17 comprises a plurality of pleats 30, resulting in a bladder insert having a plurality of resilient fluid-filled chambers. As shown in FIGS. 12A–12D, the chambers 45–50 may be independent of one another (FIG. 12D), or they may be interconnected as shown in FIG. 12C. In accordance with one embodiment of this invention, bladder insert 17 comprises at least one baffle 35 disposed within the bladder chamber.

FIGS. 18–23 show embodiments of a bladder insert for use in absorbent articles, which bladder inserts are multi-dimensional structures. FIGS. 18–21 show embodiments in which the chambers resulting from pleating of the bladder insert have different elevations and/or different cross-sectional areas. FIGS. 22 and 23 show a bladder configuration in which only the center region 60 is elevated with respect to the surrounding chambers. Similar multi-dimensional bladder inserts in accordance with this invention are also shown in FIGS. 41 and 42A–42D. In order to form such multi-dimensional bladder inserts, in additional to basic mechanical pleating, vacuum formation is employed.

Figure 38:
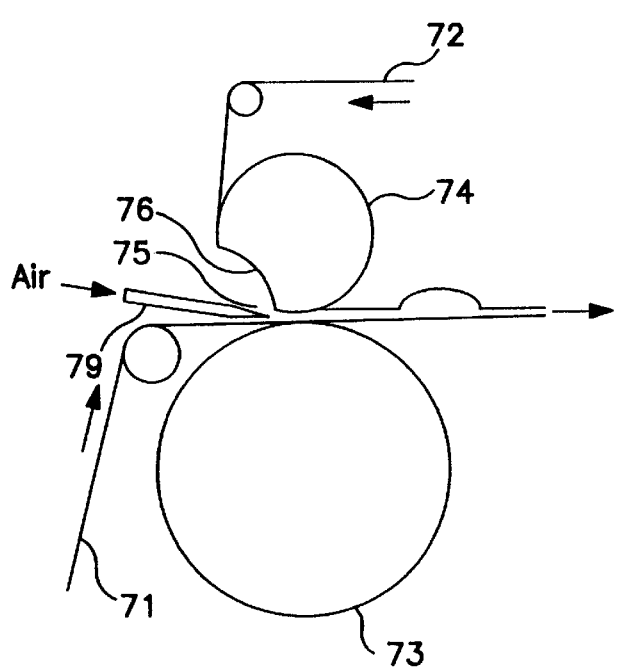
FIG. 38 is a schematic side view of a process element of a process for making a bladder insert in accordance with one embodiment of this invention.
Figure 39:
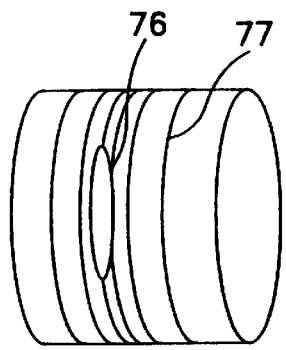
FIG. 39 is a perspective view of a vacuum section of an apparatus for vacuum forming of a bladder insert in accordance with this invention.
Figure 40:
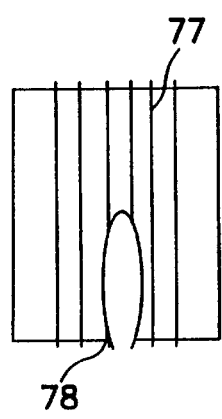
FIG. 40 is a radial cross-sectional view of the vacuum section shown in FIG. 39.
Figure 41:
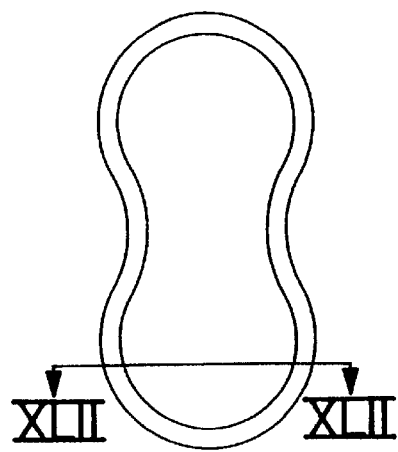
FIG. 41 is a plan view of a bladder insert produced by a vacuum forming process in accordance with one embodiment of this invention.
Figure 42A:
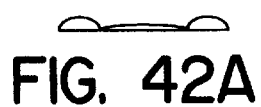
FIGS. 42A, 42B, 42C and 42D are cross-sectional views of embodiments of the bladder insert of FIG. 41 taken along the line XLII—XLII.
Figure 42B:
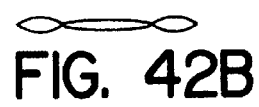
Figure 42C:
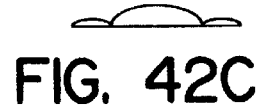
Figure 42D:

FIG. 38 shows a process for forming a bladder insert employing vacuum formation. A lower bladder material layer 71 and an upper bladder material layer 72 are conveyed into a nip 75 formed by drum 73 and vacuum/sealing drum 74. As the material layers pass into the nip 75, air or another suitable fluid is injected by injector 79 into the nip between the layers. As the layers pass through the nip, sealing bars 77, 78, shown in FIGS. 39 and 40, form a desired pattern of seals to generate a desired pattern of pleats and resilient fluid-filled chambers. Simultaneously therewith, a vacuum is applied to the upper bladder material layer by vacuum/sealing drum 74 as the material passes beneath vacuum pull region 76. Depending upon the dimensional characteristics of the vacuum pull area as well as the extent of the vacuum applied to the material, bladder inserts having a variety of multi-dimensional characteristics can be formed.

Figure 36:
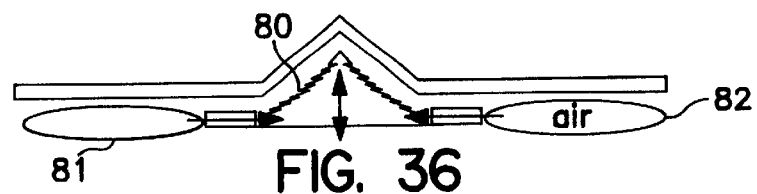
FIG. 36 is a schematic cross-sectional view of a bladder insert comprising a body-fitting mechanism in accordance with one embodiment of this invention.
Figure 37:
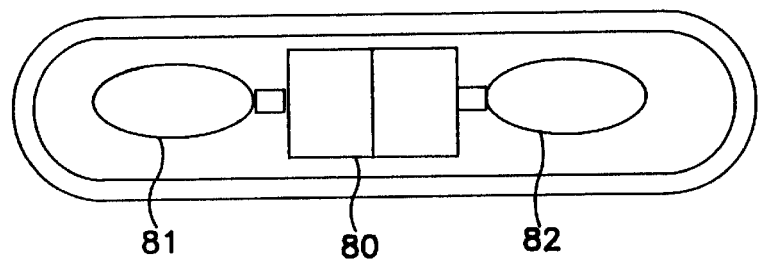
FIG. 37 is a plan view of the bladder insert of FIG. 36.

As previously stated, one result of using a bladder insert in an absorbent article is improved conformance of the absorbent article to the body of the wearer for the purpose of providing intimate contact between the absorbent article and the wearer for improved intake and distribution of body exudates. Such conformance depends upon a number of factors, not the least of which is the dimensional characteristics of the absorbent article relative to the physical characteristics, such as size and shape, of the wearer. To address this issue, one embodiment of an absorbent article in accordance with this invention comprises means for customizing the article so as to provide a better fit for individual wearers. More particularly, the bladder inserts, in addition to providing pressure against the body of the wearer, are configured to activate mechanical devices that may engage at continuous or incremental points. The mechanical devices are generally constructed of semi-rigid or rigid materials and are positioned at specific locations within the absorbent article. For example, the critical absorbency intake position of feminine care pads is the central crotch region. FIGS. 36 and 37 are diagrammatic representations of an absorbent article comprising means for customizing the article in accordance with one embodiment of this invention particularly suitable for use in feminine care pads. Such means comprises a mechanism for "pop-up" extensibility located in the central crotch region in fluid communication with said resilient fluid-filled chamber, for example a bellows-type structure 80 which, upon compression of bladder inserts 81, 82, forces a fluid, such as air, out of one or more bladder inserts 81, 82 in accordance with this invention disposed within the absorbent article and into the "pop-up" mechanism. Alternatively, bladder inserts 81, 82 may be designed to draw outside air in. In accordance with one embodiment of this invention, the mechanism may be "locked" into place to provide continual body contact. In addition, the inclusion of such a mechanism can save packaging/shipping space since the volume associated with conforming the absorbent article need not be activated until its end-use. An alternative mechanical device suitable for use as a body-fitting mechanism in accordance with one embodiment of this invention is one having lateral extension for enhancing lateral fit. It will be apparent to those skilled in the art that there are other body-fitting mechanisms which could be adapted to employ the principles of the aforementioned devices, that is devices which are activated by pressure applied to a bladder insert of an absorbent article, and such devices are deemed to be within the scope of this invention.

Figures 28A, 28B:
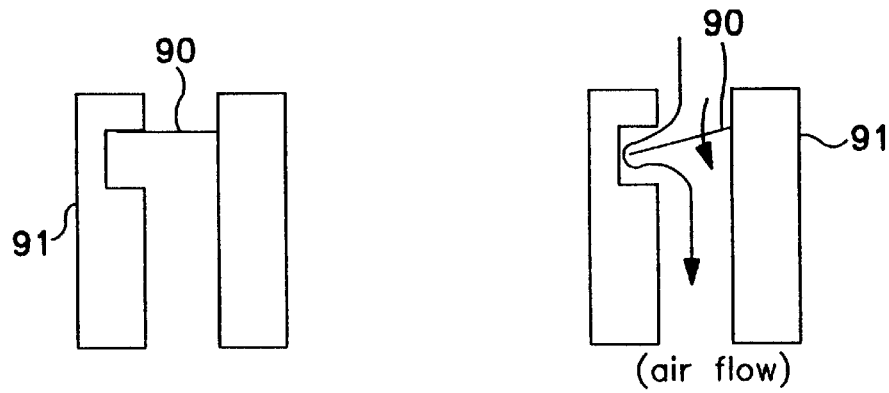
FIGS. 28A and 28B are diagrammatic views of a valve arrangement for inflation of bladder inserts in accordance with one embodiment of this invention.

Another alternative for customizing the bladder insert to conform to the body of the wearer is to provide the bladder insert with adjustable inflation means for filling the bladder insert chambers with fluid and/or adjusting the amount of fluid in the chambers to enable proper body fit. In contrast to vacuum packaged devices in which release of a plug or tape allows atmospheric air to enter a chamber, devices which employ gas-evolving material enclosed within a chamber to cause inflation or devices which employ a pump which is integral to the chamber, an absorbent article in accordance with one embodiment of this invention allows for the use of a separate device by incorporation of an appropriate valve arrangement into the absorbent article. FIGS. 28A and 28B show a valve arrangement suitable for use in absorbent articles of this invention in the form of a check valve system. Check valve 90 is disposed within fluid intake conduit 91, which, in turn, is in fluid communication with at least one chamber of a bladder insert (not shown). When fluid is introduced into the chamber of the bladder insert, check valve 90 opens, as shown in FIG. 28B to permit the flow of fluid through fluid intake conduit 91 into the chamber. When the fluid pressure within the chamber has reached a desired level, the pressure within the chamber forces check valve 90 to move to a closed position as shown in FIG. 28A.

Figure 29:
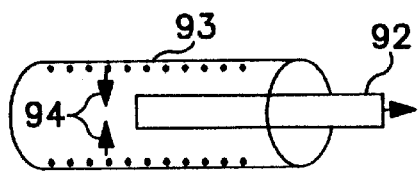
FIG. 29 is a diagrammatic view of an inflation device for inflation of a bladder insert in accordance with one embodiment of this invention.

An alternative embodiment of a valve arrangement is shown in FIG. 29. Here, a center filling element 92 is concentrically disposed within fluid intake conduit 93, which, in turn, is in fluid communication with at least one chamber of the bladder insert of an absorbent article. After inflation of the bladder insert, center filling element 92, which may be coated with an adhesive releasing material, that is a material which prevents the center filling element 92 from sticking to an adhesive, is removed and fluid intake conduit 93 is sealed by application of a compression force as indicated by arrows 94. To promote sealing of fluid intake conduit 93, the interior surface thereof may be coated with an adhesive which maintains the conduit in a sealed condition.

Figure 33:
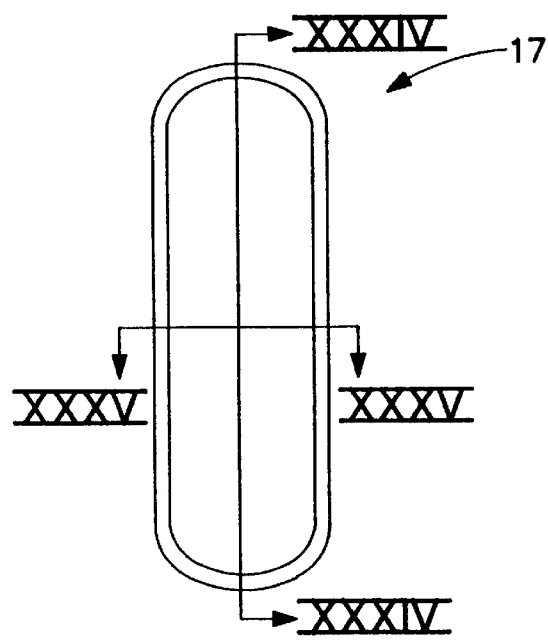
FIG. 33 is a plan view of a bladder insert comprising materials having dissimilar elasticities in accordance with one embodiment of this invention.
Figure 34:
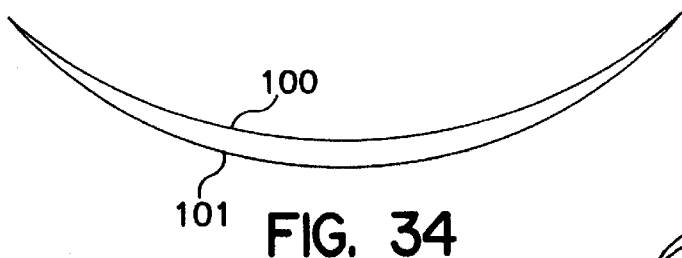
FIG. 34 is a cross-sectional view of the bladder insert of FIG. 33 taken along the line XXXIV—XXXIV.
Figure 35:
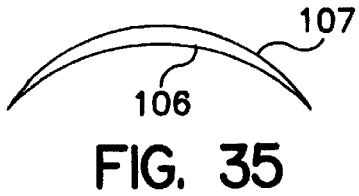
FIG. 35 is a cross-sectional view of the bladder insert of FIG. 33 taken along the line XXXV—XXXV.

In accordance with one embodiment of an absorbent article of this invention, in order to improve the fit of the article to the body of the wearer, bladder insert 17 is constructed of materials having different elasticities to generatea desired curvature in the article. FIG. 33 shows a plan view of a bladder insert 17 for an absorbent article in accordance with one embodiment of this invention employing materials of different elasticity. FIG. 34 is a cross-sectional view of the bladder insert of FIG. 33 taken along the line XXXIV—XXXIV where the material of lower elasticity 100 is disposed on top of the material of higher elasticity 101 resulting in a longitudinal upward curvature of the bladder insert. Similarly, FIG. 35 is a cross-sectional view of the bladder insert of FIG. 33 taken along the line XXXV—XXXV where the material of lower elasticity 106 is disposed below the material of greater elasticity 107 resulting in an upwards directed side-to-side curvature.

Figure 30:
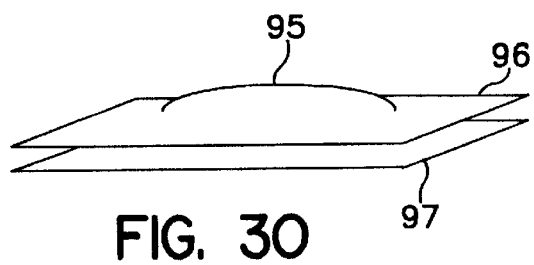
FIG. 30 is a side view of a bladder insert comprising materials having dissimilar elasticities in accordance with one embodiment of this invention.
Figure 31:
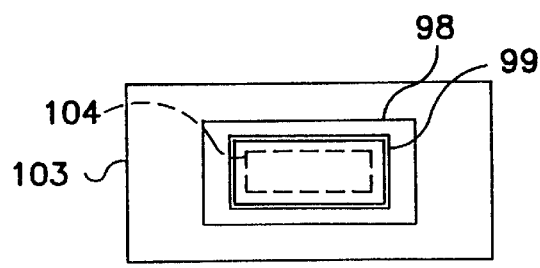
FIG. 31 is a plan view of a bladder insert comprising materials having dissimilar elasticities in accordance with one embodiment of this invention.
Figure 32:
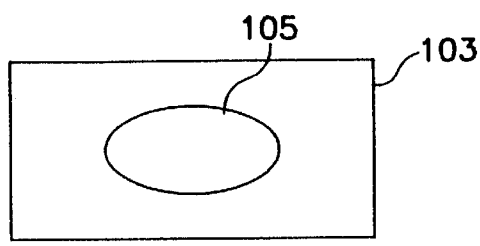
FIG. 32 is a plan view of a bladder insert comprising materials having dissimilar elasticities in accordance with one embodiment of this invention.

It will be apparent to those skilled in the art that the direction of curvature and the location of the curvature can be influenced by the position of the different materials. FIGS. 30, 31 and 32 show embodiments of a bladder insert of this invention wherein zones of materials having different elasticities are used to modify the properties in a localized region of the bladder insert. The bladder insert 17 of FIG. 30 comprising upper material layer 96 and lower material layer 97 comprises a centrally disposed bulge 95 due to a centrally disposed patch of material in upper material layer 96 having a higher elasticity than the surrounding material. Such a configuration is formed as shown in FIG. 31 where a patch 98 of a material having a given elasticity is joined by peripheral seals 99 to a material layer 103 having a lower elasticity than the patch material over an opening 104 formed by material layer 103. When material layer 103 is used as one ply or material layer of a bladder insert and the bladder insert is filled to a desired pressure with a fluid, the patch material, which constitutes a dissimilar region 105 as shown in FIG. 32, will stretch above material layer 103 forming bulge 95 as shown in FIG. 30. It will be apparent to those skilled in the art that other material dissimilarities, such as thinning of the patch material or pre-stretching of the patch material may be employed to cause different responses to a given applied pressure.

In accordance with one embodiment of this invention, fluid distribution within the absorbent articles is enhanced by application of peristaltic elements to the bladder inserts. Such peristaltic elements are generally in the form of surface modifications applied to the outer surfaces of the bladder insert. Such surface modifications work in conjunction with the bladder pressure to distribute fluid by means of peristalsis.

Figure 24:
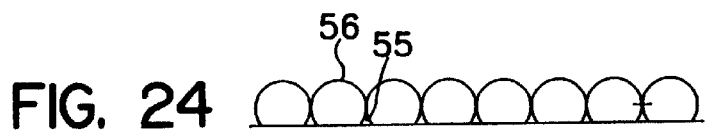
FIGS. 24, 25, 26 and 27 are cross-sectional views of a bladder insert for absorbent articles in accordance with this invention having peristaltic elements.
Figure 25:
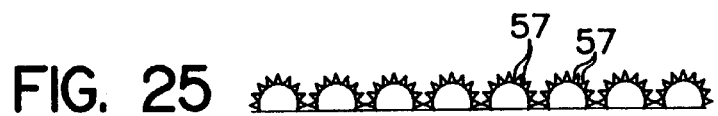
Figure 26:
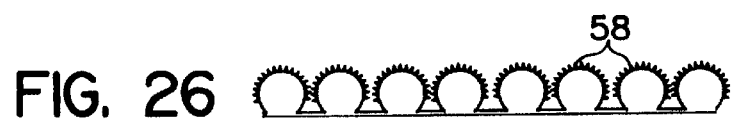
Figure 27:
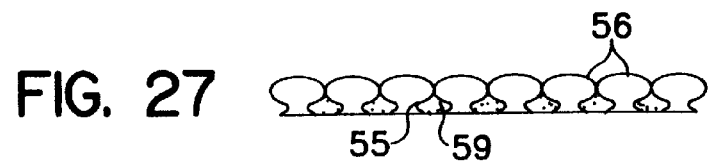
Figure 43:
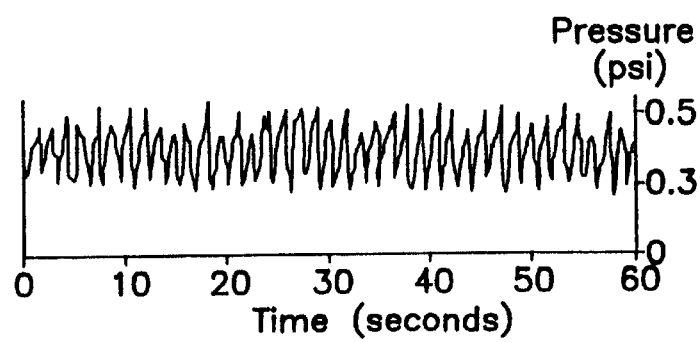
FIG. 43 is a graphic representation of the dynamic pressures applied to feminine care articles in use.

The key to the peristaltic element is the application of rhythmic pressures/forces in the direction of a finite fluid reservoir. In the case of absorbent articles in accordance with this invention, the forces needed to initiate fluid transport are created by using the dynamic forces which are applied to the absorbent articles by the human body and its motion. For example, we have found that dynamic pressures exerted to feminine care articles can alternate in a very regular way (See FIG. 43). This fact suggests that a pump-like mechanism in the center of the absorbent article can be used to improve the fluid distribution throughout the entire product. Various peristaltic elements in accordance with different embodiments of this invention are shown in FIGS. 24–27. FIG. 24 is a cross-sectional view of a multi-chamber bladder insert which forms grooves 55 in the base region of adjacent fluid-filled chambers 56. FIG. 25 is a cross-sectional view of a multi-chamber bladder insert wherein the surfaces of the resilient fluid-filled chambers 56 form a plurality of micro grooves 57. FIG. 26 is a cross-sectional view of a multi-chamber bladder insert comprising a plurality of fibers or filaments 58 disposed on the surfaces of the resilient fluid-filled chambers. And, FIG. 27 is a cross-sectional view of a multi-chamber bladder insert wherein a plurality of fibers 59 are disposed within grooves 55 in the base region of adjacent fluid-filled chambers 56.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

We claim:
1. An absorbent article comprising:
   a multi-layer material having a front section, a back section and an intermediate section connecting said front section and said back section, said multi-layer material comprising a topsheet, a backsheet and an absorbent layer disposed between said topsheet and said backsheet;
   at least one resilient fluid-filled chamber formed between an upper layer and a lower layer, the upper layer and the lower layer being of fluid-impermeable material, the chamber disposed one of in said absorbent layer and between at least a portion of said absorbent layer and said backsheet; and
   a body-fitting mechanism comprising one of semi-rigid and rigid material, the body-fitting mechanism in fluid communication with said at least one resilient fluid-filled chamber, the body fitting mechanism activatable by application of a force to said at least one resilient fluid-filled chamber, said at least one resilient fluid-filled chamber disposed remote from said body-fitting mechanism.

2. An absorbent article in accordance with claim 1, wherein said resilient fluid-filled chamber is filled with a fluid selected from the group consisting of water, air, gelatins, hydrogels, colloids, suspensions and combinations thereof.

3. An absorbent article in accordance with claim 1, wherein said fluid impermeable material is a material selected from the group consisting of thermoplastics, elastomers, polyurethane films, coated papers and combinations thereof.

4. An absorbent article in accordance with claim 3, wherein said fluid impermeable material comprises at least one of polyethylene and polypropylene.

5. An absorbent article in accordance with claim 1, wherein said lower layer is substantially coextensive with said upper layer, said upper layer and said lower layer sealingly bonded to each other around at least a portion of a material periphery.

6. An absorbent article in accordance with claim 5, wherein at least one of said layers is pleated, forming a plurality of resilient fluid-filled chambers.

7. An absorbent article in accordance with claim 5, wherein one of said upper layer and said lower layer is a substantially flat, rigid material.

8. An absorbent article in accordance with claim 5, wherein one of said upper layer and said lower layer is prestretched prior to bonding to said other material layer.

9. An absorbent article in accordance with claim 5, wherein said upper layer and said lower layer have different elasticities.

10. An absorbent article in accordance with claim 1, wherein at least one baffle is disposed in said resilient fluid-filled chamber.

11. An absorbent article in accordance with claim 1, wherein at least a portion of an outer surface of said resilient fluid-filled chamber is coated.

12. An absorbent article in accordance with claim 1 further comprising means for inflating said resilient fluid-filled chamber.

13. An absorbent article in accordance with claim 1, wherein said resilient fluid-filled chamber is vacuum formed.

14. An absorbent article in accordance with claim 1, wherein said resilient fluid-filled chamber is an oval-shaped ring.

15. An absorbent article in accordance with claim 14, further comprising a material joined to said oval-shaped ring and spanning a centrally disposed opening of said oval-shaped ring on at least one side.

16. An absorbent article comprising:
   a multi-layer material comprising a topsheet, a backsheet, and an absorbent layer disposed between said topsheet and said backsheet;
   at least one resilient fluid-filled chamber formed between an upper layer and a lower layer, the upper layer and the lower layer being of fluid-impermeable material, the chamber disposed between at least a portion of said absorbent layer and said backsheet; and
   a body-fitting mechanism comprising one of semi-rigid and rigid material, the body-fitting mechanism in fluid communication with said at least one resilient fluid-filled chamber, the body fitting mechanism activatable by application of a force to said at least one resilient fluid-filled chamber, said at least one resilient fluid-filled chamber disposed remote from said body-fitting mechanism.

17. A feminine care absorbent article comprising:
   a multi-layer material having a front section, a back section and an intermediate section connecting said front section and said back section, said multi-layer material comprising a topsheet, a backsheet and an absorbent layer disposed between said topsheet and said backsheet;
   at least one resilient fluid-filled chamber formed between an upper layer and a lower layer, the upper layer and the lower layer being of fluid-impermeable material, the chamber disposed one of in said absorbent layer and between at least a portion of said absorbent layer and said backsheet; and
   a body-fitting mechanism comprising one of semi-rigid and rigid material, the body-fitting mechanism in fluid communication with said at least one resilient fluid-filled chamber, the body fitting mechanism activatable by application of a force to said at least one resilient fluid-filled chamber, said at least one resilient fluid-filled chamber disposed remote from said body-fitting mechanism.

18. A feminine care absorbent article in accordance with claim 17, wherein at least one of said resilient fluid-filled chamber comprises at least one pleat, thereby forming a plurality of fluid-filled chambers.

19. A feminine care absorbent article in accordance with claim 17, wherein at least one of said resilient fluid-filled chamber comprises at least one pleat, thereby forming a plurality of fluid-filled chambers.

20. A feminine care absorbent article in accordance with claim 17, further comprising means for inflating said resilient fluid-filled chamber.

21. A diaper comprising:
   a multi-layer material having a front section, a back section and an intermediate section connecting said front section and said back section, said multi-layer material comprising a topsheet, a backsheet and an absorbent layer disposed between said topsheet and said backsheet;
   at least one resilient fluid-filled chamber formed between an upper layer and a lower layer, the upper layer and the lower layer being of fluid-impermeable material, the chamber disposed between at least a portion of said absorbent layer and said backsheet; and a body-fitting mechanism comprising one of semi-rigid and rigid material, the body-fitting mechanism in fluid communication with said at least one resilient fluid-filled chamber, the body fitting mechanism activatable by application of a force to said at least one resilient fluid-filled chamber, said at least one resilient fluid-filled chamber disposed remote from said body-fitting mechanism.

* * * * *